US00PP13763P29

(12) United States Plant Patent
Klemm

(10) Patent No.: US PP13,763 P2
(45) Date of Patent: May 6, 2003

(54) GERANIUM PLANT NAMED 'KLEP01007'

(75) Inventor: Nils Klemm, Stuttgart (DE)

(73) Assignee: Klemm + Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 10/171,832

(22) Filed: Jun. 17, 2002

(51) Int. Cl.[7] ..... A01H 5/00

(52) U.S. Cl. ..... Plt./328

(58) Field of Search ..... Plt./328, 329

*Primary Examiner*—Kent Bell
(74) *Attorney, Agent, or Firm*—C. A. Whealy

(57) ABSTRACT

A new and distinct cultivar of Zonal Geranium plant named 'KLEP01007', characterized by its upright and uniform plant habit; freely basal branching habit; dark green-colored leaves; freely flowering habit; dark pink-colored flowers; and upright and strong red brown peduncles.

1 Drawing Sheet

BOTANICAL CLASSIFICATION/CULTIVAR DESIGNATION

*Pelargonium×hortorum* cultivar 'KLEP01007'.

BACKGROUND OF THE INVENTION

The present invention relates to a new and distinct cultivar of Zonal Geranium plant, botanically known as *Pelargonium×hortorum*, and hereinafter referred to by the name 'KLEP01007'.

The new Zonal Geranium is a product of a planned breeding program conducted by the Inventor in Stuttgart, Germany. The objective of the breeding program was to develop new Zonal Geraniums with uniform plant habit, upright peduncles, and interesting flower and foliage colors.

The new Zonal Geranium originated from a cross made by the Inventor in 1997 of the *Pelargonium×hortorum* cultivar Klelad, disclosed in co-pending U.S. plant patent application Ser. No. 09/250,019, as the female, or seed, parent with the *Pelargonium×hortorum* cultivar Klecardi, not patented, as the male, or pollen, parent. The cultivar KLEP01007 was discovered and selected by the Inventor as a flowering plant within the progeny from this cross in a controlled environment in Stuttgart, Germany, in 1997.

Asexual reproduction of the new cultivar by terminal cuttings taken at Stuttgart, Germany has shown that the unique features of this new Zonal Geranium are stable and reproduced true to type in successive generations of asexual reproduction.

SUMMARY OF THE INVENTION

The following traits have been repeatedly observed and are determined to be the unique characteristics of 'KLEP01007'. These characteristics in combination distinguish 'KLEP01007' as a new cultivar and distinguish it from other known Zonal Geranium cultivars:

1. Upright and uniform plant habit.
2. Freely basal branching habit.
3. Dark green-colored leaves.
4. Freely flowering habit.
5. Dark pink-colored flowers.
6. Upright and strong red brown peduncles.

Plants of the new Zonal Geranium differ primarily from plants of the female parent, the cultivar Klelad, in the following characteristics:

1. Plants of the new Zonal Geranium are more vigorous and not as compact as plants of the cultivar Klelad.

2. Plants of the new Zonal Geranium have longer peduncles than plants of the cultivar Klelad.

Plants of the new Zonal Geranium differ primarily from plants of the male parent, the cultivar Klecardi, in the following characteristics:

1. Plants of the new Zonal Geranium have darker green foliage than plants of the cultivar Klecardi.

2. Plants of the new Zonal Geranium flower earlier than plants of the cultivar Klecardi.

3. Plants of the new Zonal Geranium have dark pink-colored flowers whereas plants of the cultivar Klecardi have purple-colored flowers.

The new Zonal Geranium can be compared to plants of the cultivar Klecerol, disclosed in U.S. Plant Pat. No. 7,410. However, in side-by-side comparisons conducted in Stuttgart, Germany, plants of the new Zonal Geranium differed from plants of the cultivar Klecerol in the following characteristics:

1. Plants of the new Zonal Geranium were not as vigorous as plants of the cultivar Klecerol.

2. Plants of the new Zonal Geranium had darker green foliage than plants of the cultivar Klecerol.

3. Leaves of the new Zonal Geranium did not have a distinct zonation pattern whereas leaves of the cultivar Klecerol had a distinct zonation pattern.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Flower and foliage colors in the photograph may differ slightly from the color values cited in the detailed botanical description which accurately describe the colors of the new Zonal Geranium. The photograph comprises a side perspective view of a typical flowering plant of 'KLEP01007' grown in a 12-cm container.

DETAILED BOTANICAL DESCRIPTION

The cultivar KLEP01007 has not been observed under all possible environmental conditions. The phenotype may vary somewhat with variations in environment, such as temperature and light intensity, without, however, any variance in genotype.

The aforementioned photographs, following observations, and averaged measurements describe plants that were planted in January in 12-cm pots in Stuttgart, Germany, and grown for about three months under commercial practice in a glass-covered greenhouse with day temperatures about 18 to 22° C., night temperatures about 14 to 17° C., and light levels about 20,000 to 55,000 lux. Plants used for the photographs and detailed botanical description were about 85 days old.

In the following description, color references are made to The Royal Horticultural Society Colour Chart except where general terms of ordinary dictionary significance are used.

Botanical classification: *Pelargonium×hortorum* cultivar KLEP01007.

Parentage:

*Female parent.*—*Pelargonium×hortorum* cultivar Klelad, disclosed in co-pending U.S. plant patent application Ser. No. 09/250,019.

*Male parent.*—*Pelargonium×hortorum* cultivar Klecardi, not patented.

Propagation:

*Type cutting.*—Terminal cuttings.

*Time to initiate roots.*—Summer: About 9 days at 22° C. Winter: About 12 days at 18 to 20° C.

*Time to develop roots.*—Summer: About 16 days at 22° C. Winter: About 18 days at 18 to 20° C.

*Root description.*—Fine, freely branching, and white in color.

Plant description:

*General appearance.*—Upright and uniform plant habit; densely foliated.

*Crop time.*—About three months are required to produce a finished flowering plant in 12-cm container.

*Growth and branching habit.*—Moderately vigorous. Freely basal branching, about four or five lateral branches develop without pinching, that is, removal of terminal apices.

*Plant height* (*to top of flower umbels*).—About 23.5 cm.

*Plant height* (*to top of foliar plane*).—About 18 cm.

*Plant width.*—About 21 cm.

*Lateral branches.*—Length: About 8 cm. Internode length: About 1 cm. Texture: Rough. Color: 139C.

*Foliage description.*—Arrangement: Alternate, simple. Quantity of leaves per lateral branch: About 6 or 7. Length: About 5 cm. Width: About 8 cm. Shape: Reniform. Apex: Rounded. Base: Lobed, overlapping. Margin: Crenate. Venation pattern: Palmate. Texture, upper and lower surfaces: Rough. Color: Young and fully expanded foliage, upper surface: 137A; no distinct zonation pattern. Young and fully expanded foliage, lower surface: 137C. Venation, upper and lower surfaces: 139C. Petiole: Length: About 6 cm. Diameter: About 3 mm. Color, upper and lower surfaces: 143B.

Flower description:

*Flower arrangement.*—Dark pink-colored flowers arranged in rounded hemispherical umbels arising from apical leaf axils. Umbels displayed above the foliage on upright and strong peduncles. Flowers semi-double in form, rounded and cup-shaped. Umbels persistent, flowers not persistent. Flowers not fragrant.

*Quantity of flowers.*—Freely flowering. At full flower, plants have about 6 to 8 open umbels and about 3 to 5 developing umbels and each umbel has about 20 to 35 flowers and flower buds per umbel.

*Flowering season.*—Year-round under greenhouse conditions. In the garden, flowering is continuous from spring until fall.

*Flower longevity.*—Flowers last about 6 to 12 days on the plant.

*Umbel size.*—Height: About 10 cm. Diameter: About 8 to 12 cm.

*Flower size.*—Diameter: About 4 cm. Depth (height): About 1.5 cm.

*Flower buds.*—Length: About 1.2 cm. Diameter: About 7 mm. Shape: Elliptic. Color: Towards the apex, 139C; towards the base, 184B.

*Petals.*—Quantity per flower: About 6 to 8. Length: About 2.5 cm. Width: About 2 cm. Shape: Ovate. Apex: Rounded. Base: Attenuate. Margin: Entire. Texture, upper and lower surfaces: Smooth, velvety. Color: When opening and fully opened, upper surface: 68A; towards base, 73B to 73D; color does not fade with subsequent development. When opening and fully opened, lower surface: 73B; towards base, 73C to 73D. Venation, upper and lower surfaces: 68A.

*Petaloids.*—Quantity per flower: About 1 to 5. Length: About 3 to 10 mm; irregular in size. Width: About 1 to 5 mm; irregular in size. Shape: Variable, irregular. Apex: Mostly rounded. Base: Attenuate. Margin: Mostly entire. Texture, upper and lower surfaces: Smooth, velvety. Color: When opening and fully opened, upper surface: 68B; color does not fade with subsequent development. When opening and fully opened, lower surface: 73C. Venation, upper and lower surfaces: 68B.

*Sepals.*—Quantity per flower: Five, arranged in a single whorl. Length: About 9 mm. Width: About 5 mm. Shape: Elliptic. Apex: Narrowly acute. Margin: Entire. Texture, upper and lower surfaces: Pubescent, velvety. Color, upper and lower surfaces: Towards the apex, 139C; towards the base, 184B.

*Peduncle* (*umbel stem*).—Length: About 14.5 cm. Diameter: About 5 mm. Angle: Erect. Strength: Strong. Texture: Rough. Color: 139C overlain with 184B.

*Pedicel* (*individual flower stem*).—Length: About 2.5 cm. Diameter: About 1.5 mm. Angle: Erect. Strength: Moderately strong. Texture: Rough. Color: 184B.

*Reproductive organs.*—Androecium: Anther quantity per flower: About five. Anther length: About 3 mm. Anther shape: Ovate. Anther color: 49A. Pollen amount: Moderate. Pollen color: 33A. Gynoecium: Pistil quantity per flower: One. Pistil length: About 1 cm. Stigma shape: Five-parted, star-shaped. Stigma color: 57C. Style length: About 4 mm. Style color: 57D. Ovary color: 149D.

*Seed.*—Length: About 3 to 6 mm. Diameter: About 1.5 to 2 mm. Shape: Ovoid. Color: Brown.

Disease tolerance: Plants of the new Zonal Geranium have been observed to be tolerant to pathogens common to Pelargonium, such as Botrytis.

Weather tolerance: Plants of the new Zonal Geranium have been observed to tolerate rain, wind, and temperatures from 8 to 32° C.

It is claimed:

1. A new and distinct cultivar of Zonal Geranium plant named 'KLEP01007', as herein illustrated and described.

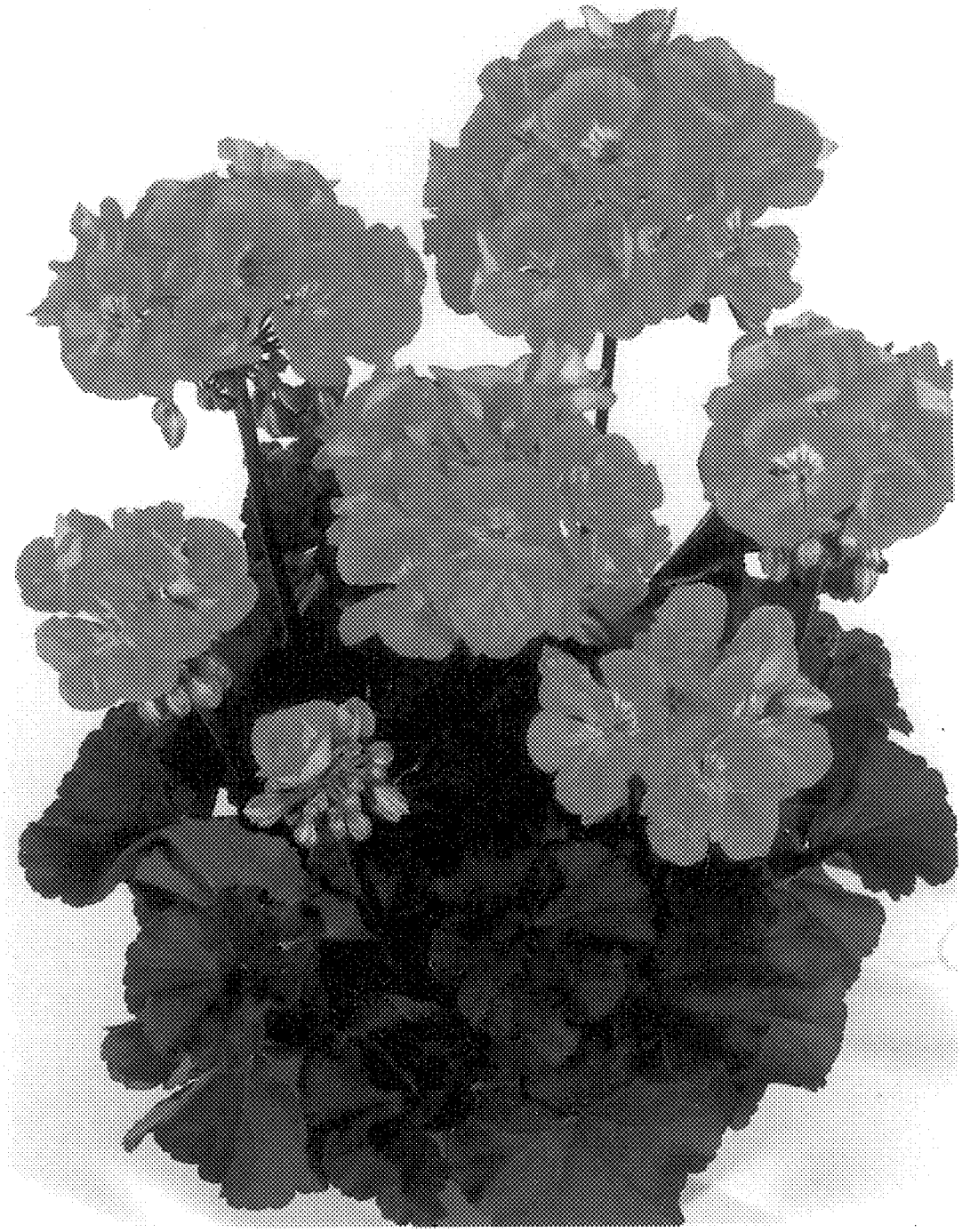

* * * * *